(12) United States Patent
Hommann et al.

(10) Patent No.: US 7,566,324 B2
(45) Date of Patent: Jul. 28, 2009

(54) INJECTION DEVICE COMPRISING A NEEDLE COVER

(75) Inventors: Edgar Hommann, Grossaffoltern (CH); Hans Himbert, Bromma (SE); Ulrika Vejbrink, Hagersten (SE)

(73) Assignee: TecPharma Licensing AG, Burgdorf (DE)

( * ) Notice: Subject to any disclaimer, the term of this patent is extended or adjusted under 35 U.S.C. 154(b) by 0 days.

(21) Appl. No.: 11/404,384

(22) Filed: Apr. 14, 2006

(65) Prior Publication Data

US 2007/0078382 A1  Apr. 5, 2007

Related U.S. Application Data

(63) Continuation of application No. PCT/CH2004/000617, filed on Oct. 8, 2004, which is a continuation-in-part of application No. 10/687,517, filed on Oct. 16, 2003.

(30) Foreign Application Priority Data

Oct. 16, 2003 (DE) .............................. 103 48 185
Oct. 16, 2003 (DE) .............................. 103 48 186

(51) Int. Cl.
*A61M 5/32* (2006.01)
*A61M 5/00* (2006.01)

(52) U.S. Cl. ................... 604/198; 604/197; 604/263

(58) Field of Classification Search ............... 604/500, 604/506, 110, 181, 187, 192–199, 232, 240–243, 604/263

See application file for complete search history.

(56) References Cited

U.S. PATENT DOCUMENTS

| 5,634,906 | A | 6/1997 | Smedley et al. |
| 5,681,291 | A * | 10/1997 | Galli ........................ 604/192 |
| 6,183,446 | B1 | 2/2001 | Jeanbourquin |
| 7,118,552 | B2 * | 10/2006 | Shaw et al. ................ 604/110 |
| 2002/0087124 | A1 | 7/2002 | Grabis et al. |
| 2002/0169421 | A1 * | 11/2002 | McWethy et al. ........... 604/192 |
| 2003/0040716 | A1 | 2/2003 | Geiser et al. |

FOREIGN PATENT DOCUMENTS

EP  1 262 207 A1  12/2002

* cited by examiner

*Primary Examiner*—Kevin C Sirmons
*Assistant Examiner*—Bhisma Mehta
(74) *Attorney, Agent, or Firm*—Dorsey & Whitney LLP; David E. Bruhn

(57) ABSTRACT

An injection device including a needle cover, a casing, an injection mechanism, and a needle holder including an injection needle, wherein the needle cover is carried by the casing such that it can be moved, against a restoring force, from a protecting position, past an injection position, and into an assembling position. In the protecting position, the needle cover extends beyond the skin penetrating tip of the injection needle and, in the injection position, the needle cover is short of the tip. In the assembling position, the needle cover allows access to the needle holder, whereby the needle holder can be gripped and connected to or detached from the casing.

17 Claims, 6 Drawing Sheets

INJECTION DEVICE COMPRISING A NEEDLE COVER

CROSS-REFERENCE TO RELATED APPLICATION(S)

This application is a continuation of International Patent Application PCT/CH2004/000617, filed on Oct. 8, 2004, which claims priority to German Application 103 48 185.0, filed on Oct. 16, 2003, German Application 103 48 186.9, filed on Oct. 16, 2003, and U.S. patent application Ser. No. 10/687,517, filed on Oct. 16, 2003, now published as U.S. Publication No. 2005/0085776 on Apr. 21, 2005, the entire contents of which applications are incorporated by reference herein.

BACKGROUND

The present invention relates to devices for delivering, injecting, dispensing or administering substances, and to methods of making and using such devices. More particularly, it relates to an injection device comprising a needle cover for an injection needle which may be or is already affixed to the injection device at one end thereof, which may be referred to as the front end. The injection device may be used in self-administering an injectable product, for example insulin, a growth hormone or an osteoporosis medicine. In some embodiments, the injection device may be an injection pen.

The injection needle of an injection device poses a danger of injury, such as inadvertent sticks, contamination, etc., for example when exchanging the injection needle. Needles also may cause fear (needle phobia) in many patients who administer the product to themselves by injection, which can very well be the cause of an incorrect injection or at least a less than optimal injection. In order to reduce fear of the injection needle, injection devices are often provided with a needle blind or cover which surrounds and hides the needle in a protecting position, such that the user of the injection device in question cannot see the needle. The needle blind is usually held in the protecting position by a mechanical spring. For injecting, the user places the injection device onto the skin at the injection point and presses it against the skin, such that the needle blind is moved out of the protecting position, against the force of the spring, and the injection needle is simultaneously introduced into the body tissue. When the injection needle is removed from the body tissue, the needle blind automatically moves back into the protecting position due to the restoring force of the spring. In addition to the needle blind, a needle protector for injection devices is also known which is at least not primarily intended solely as a blind, but also to provide protection for the user against injuries from the injection needle. In the protecting position cited, the needle protector is locked and cannot be moved, for example, rearwardly, by a pressure force alone acting in the rearward direction, but only by destruction or by conscious, additional handling which releases a latch which is active in the protecting position. The needle protector can in principle expose the needle to view or, however, can also have the capacity of a blind, in addition to the function of protecting access.

U.S. Pat. No. 6,033,387 discloses an injection device embodied as a simple syringe with a protector protector. The needle protector encases the syringe completely and forms, so to speak, an outer casing for the syringe as a whole. When, after an injection, the needle protector has been moved into its protecting position by hand, it cannot be moved back out of the protecting position, or at least cannot be moved back into an assembling position until the syringe has been removed. In particular, there exists no injection position for the needle protector from which it automatically moves into the protecting position when the pressure is relieved.

In some embodiments, injection devices such as those to which the present invention relates may comprise a container holder into which a container filled with the product to be injected is inserted and, once consumed, replaced by a new container. In many cases, the container is an ampoule filled by the product manufacturer which is sealed at one end by an axially shifting piston and at another end by a sealing element. Since such injection devices are provided for an extended period of use with a number of consecutive product containers, the injection needles are also exchanged from time to time, for example together with the container. To this end, the injection needle is affixed to a needle holder connected to the injection device. When the needle holder is connected to the injection device, the injection needle pierces the sealing element of the container via a proximal (or rear or rearwardly facing) needle tip, such that a fluidic connection between the interior of the container and the injection needle is established.

Needle covers of this type, such as are known from, for example, DE 197 55 125 A1 and DE 100 09 816 A1, have a drawback in that they cannot be connected to the injection device until the needle holder has already been connected to the injection device. This has the result that the user has to affix the needle cover to the injection device while the injection needle is exposed and therefore has to work against the exposed injection needle, so to speak, when affixing the needle cover.

SUMMARY

Instead of the terms needle protector and needle blind, the term needle cover is used undifferentiated herein, and—if nothing is said specifically as to a protecting function or a blind or hiding function—is intended to refer to needle blinding or covering structures and/or functions, needle protector or protection and/or access structures and/or functions, and/or combinations thereof.

One object of the present invention is to provide an injection device comprising a needle cover, in which the danger of a needle prick while affixing a needle holder to the injection device and/or detaching a needle holder from the injection device is reduced.

In one embodiment, the present invention comprises an injection device comprising a needle cover, a casing, and a needle holder comprising an injection needle, wherein the needle cover is carried by the casing so it can be moved, against a restoring force, from a protecting position, past an injection position, and into an assembling position. In the protecting position, the needle cover extends beyond the skin penetrating tip of the injection needle and, in the injection position, the needle cover is short of the tip. In the assembling position, the needle cover is adapted to permit a user to grasp the needle holder so it can be connected to or detached from the casing.

In one embodiment, the present invention comprises a needle cover for use with an injection device comprising a casing and a needle holder comprising an injection needle, wherein the needle cover is carried by the casing so it can be moved, against a restoring force, from a needle protecting position, past an injection position, and into an assembling position, wherein in the needle protecting position, the needle cover extends beyond a skin penetrating tip of the injection needle and, in the injection position, the needle cover is short of the tip and, in the assembling position, the needle cover allows for gripping the needle holder so the needle holder can be connected to or detached from the casing.

In some embodiments, injection devices such as those to which the present invention relates include a casing which forms a receptacle for a container containing an injectable product or directly forms such a container itself. The injection devices further include a conveying means for the product, and a needle holder including an injection needle and a needle cover. The needle holder may be connected or is connected to the casing, irrespective of whether the casing forms the product container itself or the product container is a separate, in some embodiments, exchangeable, container which the casing accommodates. In the case of a product container accommodated by the casing, it is in principle also conceivable that the needle holder may be connected or is connected directly to such a container. The injection needle is held by the needle holder such that it is fluidically connected to the inner space of the container when the needle holder is connected to the container or to the casing. When the needle holder is connected in this way, the product is delivered out of the container through the injection needle by a conveying action of the conveying means.

In some embodiments, the needle holder can be formed in the fashion of known needle holders in which an injection needle is connected to the needle holder in a middle needle section, and extends from both sides of the needle holder, i.e., on the skin-penetrating injection side and on the side of the needle holder to be connected to the casing or the container. The injection needle does not, however, necessarily have to extend from both sides.

In some embodiments, the needle cover is mounted by the casing such that it can be moved back and forth in the distal (forward) and proximal (rearward) direction. The needle cover is loaded with a restoring force in the distal direction. Influenced by the restoring force, it assumes a protecting position in which it extends beyond the tip of the injection needle, when the needle holder is connected to the casing or the container. The needle cover can be moved in a rearward direction, against the restoring force, out of the protecting position into an injection position, and in a direction beyond the injection position into an assembling position. In the injection position, the tip of the injection needle protrudes beyond the end of the needle cover. In order to move the needle cover rearwardly, it must be loaded with a force opposing and exceeding the restoring force. Typically, such a force acts when the injection needle is introduced into a body tissue, namely due to the resistance of the surface of the tissue against which the needle cover is pressed during the injection. If, in the injection position, the force acting in the rearward direction abates, then the needle cover automatically moves back in the opposite direction under the influence of the restoring force. In this respect, the equilibrium of the forces, i.e., of the restoring force and the opposing force, prevails in the injection position. The injection position is therefore not fixedly predetermined, but depends on the depth of penetration of the injection needle during the injection. It is, however, defined in as much as that the injection needle can penetrate into the tissue during the injection to the extent of the needle section which protrudes beyond the needle holder. The end of the needle cover and the end of the needle holder are therefore level during the injection.

In accordance with one embodiment of the present invention, the needle cover can be moved against the restoring force into an assembling position. In the assembling position, it releases access to the needle holder, such that the needle holder can be gripped and connected to the casing and/or detached from the casing by hand. The needle cover can therefore be connected to the casing before attaching the needle holder, even when assembling or manufacturing the injection device. The needle cover does not have to be removed to exchange the injection needle.

In some preferred embodiments, the needle cover is an integral component of the injection device and cannot be detached from the injection device, i.e. from its casing, by the user, generally the patient administering the product to him/herself, which reduces the danger of incorrect assembly. In particular, however, the danger of injury from the injection needle while assembling and/or disassembling the needle holder, for example while exchanging the injection needle, is reduced, since the user does not have to assemble the needle cover when the injection needle is exposed.

In its assembling position, the needle cover is sufficiently short of the end of the needle holder in the rearward direction that the user can comfortably grip the needle holder from the side, i.e., perpendicular to the longitudinal direction of the needle, with his or her fingers and perform the necessary handling for assembling and/or disassembling the needle holder.

In some preferred embodiments, as already mentioned, the casing forms a receptacle for a product container which is exchangeable. To this end, the casing includes a container holder which forms an accommodating chamber for the container. A stopper for the container is formed in the accommodating chamber, against which the container contacts in the forward or front direction. In some preferred embodiments, the container holder secures the container in the accommodating chamber against movements perpendicular to the forward and rearward directions. The accommodating chamber may be open at a rear end of the chamber, such that the container introduced into the accommodating chamber, up to the stopper. It would also, however, be possible to provide the accommodating chamber with the opening for the container at the other end or, in principle, also on the side. The container holder may be dimensionally stable in its own right, i.e., not flexible but rigid.

In accordance with some preferred embodiments, the needle cover is supported in the rearward direction on a container holder such that the restoring force acts between the needle cover and the container holder, as an elasticity force. Instead of being directly supported on the container holder, the needle cover can in principle also be supported on another casing part of the injection device which is connected to the container holder. The needle cover may be guided slidably on the container holder, i.e., the container holder forms a sliding guide for the needle cover as it moves.

In some preferred embodiments, a restoring means which generates the restoring force generates the restoring force as an elasticity force. Due to its simplicity, the elasticity force is generated by a mechanical spring, for example by a spiral spring, which is biased or pressurised, at least in the assembling position and injection position and, in some preferred embodiments, also in the protecting position. In principle, it would also be possible to generate the elasticity force by compressing a gas, such as air.

In some embodiments, to facilitate assembling and/or disassembling the needle holder, the needle cover is prevented, in the assembling position, from moving in the forward direction by means of a locking means acting between the needle cover and the casing, such that the user does not have to hold the needle cover against the restoring force him or herself. For the lock, the casing is provided with a first locking element and the needle cover with a second locking element. When the needle cover is in the assembling position, the locking elements are in a locking mesh or connection which holds the needle cover in the assembling position against the restoring force. A number of first and second locking elements, each in pairs, can be in a locking mesh. If a number of first and second locking elements are provided, it may be preferred that two first locking elements and two second locking elements are provided and each first and second of the locking elements, in pairs, are in a locking mesh or connection with each other. The two locking element pairs are expediently arranged on sides of the injection device which are diametrically opposite each other with respect to an axial. The locking mesh can be based solely on a frictional lock between the locking elements, however the locking mesh may also be based on a positive lock, or, as applicable, a combined frictional and positive lock.

In some preferred embodiments, the injection device includes an unlocking element which can be operated by the user and which, when operated, releases the locking mesh. The unlocking element can be directly formed by a sleeve body which forms the needle cover, if, for example, the user can grip a sleeve section of such a sleeve body, in the assembling position. In addition to such a covering sleeve or sleeve-shaped covering body, the needle cover may include an unlocking element which can be moved relative to such a covering sleeve or sleeve-shaped covering body. If a number of locking element pairs are provided, one such unlocking element may be provided per pair. In some preferred embodiments, the unlocking element is formed as a push-key which is pressed relative to the covering sleeve or sleeve-shaped covering body in order to release the locking mesh or connection.

In one preferred embodiment, at least one of the locking elements can be moved out of locking mesh against an elasticity force and is automatically moved into the locking mesh due to the elasticity force when the needle cover is moved into the assembling position. The at least one locking element which can be moved out of locking mesh against an elasticity force is itself elastic. It may be dimensionally elastic, such that it simultaneously applies the elasticity force for pre-latching into the locking mesh itself and on the other hand exhibits the necessary rigidity for a positive lock. In some preferred embodiments, the elastic locking element may comprise a bending tongue comprising either a projecting cam or a recess or breach into which the other locking element protrudes in the locking mesh.

In some preferred embodiments, the casing includes a cladding structure which surrounds at least an axial section of the needle cover when the needle cover is in the assembling position. When the needle cover moves into the assembling position, at least said axial section of the needle cover enters the cladding structure of the casing. The cladding structure surrounds a section of the container holder as already explained, wherein an annular space remains between the cladding structure and that section of the container holder and at least said axial section of the needle cover is accommodated in said space, in its assembling position. In some preferred embodiments, an axial section of the needle cover also protrudes into the cladding structure of the casing and the formed annular space in the protecting position. In the assembling position, it is completely or almost completely accommodated in the annular space, such that it closes flush with the cladding structure of the casing or only protrudes beyond the end of the cladding structure of the casing by a short axial section. The restoring means can be accommodated in the annular space.

It may also be noted with respect to the conveying means that, in one preferred embodiment, it includes a piston accommodated in the container, wherein a stroke of said piston delivers product from the container through the injection needle. The piston stroke may be made in one or both of the axial directions, including in the forward, delivery or injecting direction.

In some embodiments, the injection device is one which allows a predetermined product dosage or a number of respectively selectable product dosages to be administered a number of times. For this purpose, such an injection device includes a dosing means which meshes or couples with the conveying means, for example in a mechanical connection, which causes the product dosage to be set by a dosing movement of the dosing means, wherein said product dosage can be conveyed by means of the conveying means when the conveying means is operated. In one preferred embodiment of the conveying means as a piston conveying means, this can be the length of the piston stroke or, in the case of a piston stroke which is, for example, always of the same length, the setting of a slight gap between a rear side of the piston and an end of a piston rod axially facing the rear side of the piston, which initially travels the slight gap up to the piston when a conveying stroke is performed, and then slaves the piston for the remaining stroke.

In addition to embodiments of injection devices as such, the present invention also comprises a method for affixing a needle holder, which holds an injection needle, to a forward end (which also may be referred to as the distal end) of an injection device, and furthermore a method for detaching a needle holder, which holds an injection needle, from an injection device. The injection device is provided with a needle cover which in a protecting position surrounds the injection needle up to and beyond a tip of the needle when the needle holder is affixed to the injection device, and which can be shifted out of the protecting position against a restoring elasticity force, towards an end of the injection device beyond the end of the needle holder, up to an assembling position.

When affixing the needle holder, the needle cover is moved from the protecting position into the assembling position in a first step, and a locking mesh is established which holds the needle cover in the assembling position, against the elasticity force. In some preferred embodiments, the locking mesh is established automatically when the needle cover has reached the assembling position. While the needle cover is situated in the locked assembling position, the needle holder is affixed to the end of the injection device. It is, for example, screwed onto the end of the injection device. The needle holders are usually provided with a protecting cap which protectively surrounds the needle section protruding beyond the needle holder, and protects the user from needle pricks. When using such a needle holder, the protecting cap is removed once the needle holder has been affixed, such that the injection needle is exposed. If, furthermore, another protecting cap also surrounds the needle holder, then this other protecting cap is also removed. The locking mesh is then released, such that the needle cover is automatically moved into the protecting position by the influence of the restoring elasticity force.

For detaching the needle holder, the needle cover is moved from the protecting position into the assembling position—and therefore, in some embodiments, automatically, into the locking mesh—in a first step, as for affixing the needle holder. With the needle cover in the assembling position, the needle holder is detached from the end of the injection device, and disposed of. A protective cap is affixed, e.g., plugged, onto the needle holder, before the needle holder is detached, while the needle cover is in the assembling position, in order to protect the user from needle pricks.

In another embodiment of the present invention, a guide or guiding means may be provided on an interior side of a sleeve serving as needle cover, to guide when the injection needle or a cap for the injection needle is placed onto or removed from the product container. To this end, grooves or projections can be provided, along which corresponding, complementary grooves or projections on an injection needle unit or cap can be guided onto the product container or its holder. In another embodiment, it is also possible to arrange the injection needle unit or the cap in a selected rotational position with respect to the product container. The rotational position is maintained by the guiding means. The needle unit or the cap is inserted into or attached to the guide of the sleeve in this position. By retracting the sleeve, together with the needle unit or cap, in the axial direction towards the product container, the needle unit or cap is then guided onto the container or its holder in the selected rotational position, until it is fixed on the product container.

In some embodiments of the needle protector in accordance with the present invention the needle can be attached to the product container or its holder first and the needle is immediately protected by the needle protector, and the product container does not have to be inserted into the injection device first and then the needle attached. Such a procedure may be advantageous in the case of a double-chamber ampoule, in which the product to be administered is not mixed until just before it is administered, since subsequently placing the needle onto an ampoule which has already been inserted into the injection device could exert an additional pressure on the double-chamber ampoule which can have a disruptive effect on the mixing properties.

In some embodiments, after a product container has been inserted into the casing of the injection device, a further casing part for protecting the injection needle or a user does not have to be added. The injection needle of the injection device is therefore protected during the entire process of exchanging the product container and the process of administering the product dosage.

DETAILED DESCRIPTION OF THE DRAWINGS

Figure 1:
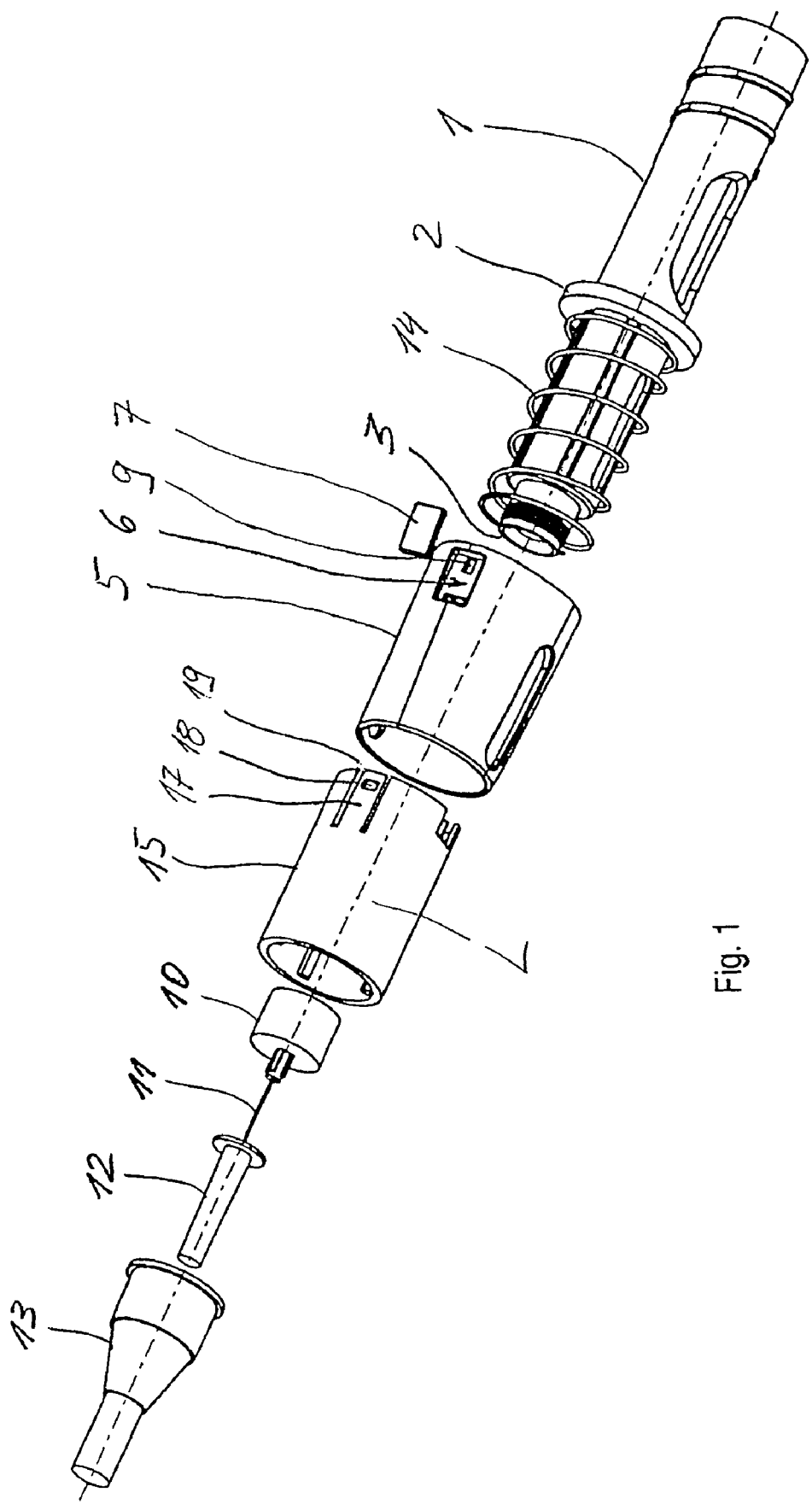
FIG. 1 shows a part of an injection device in accordance with one embodiment of the present invention, in an exploded view.
Figure 2:
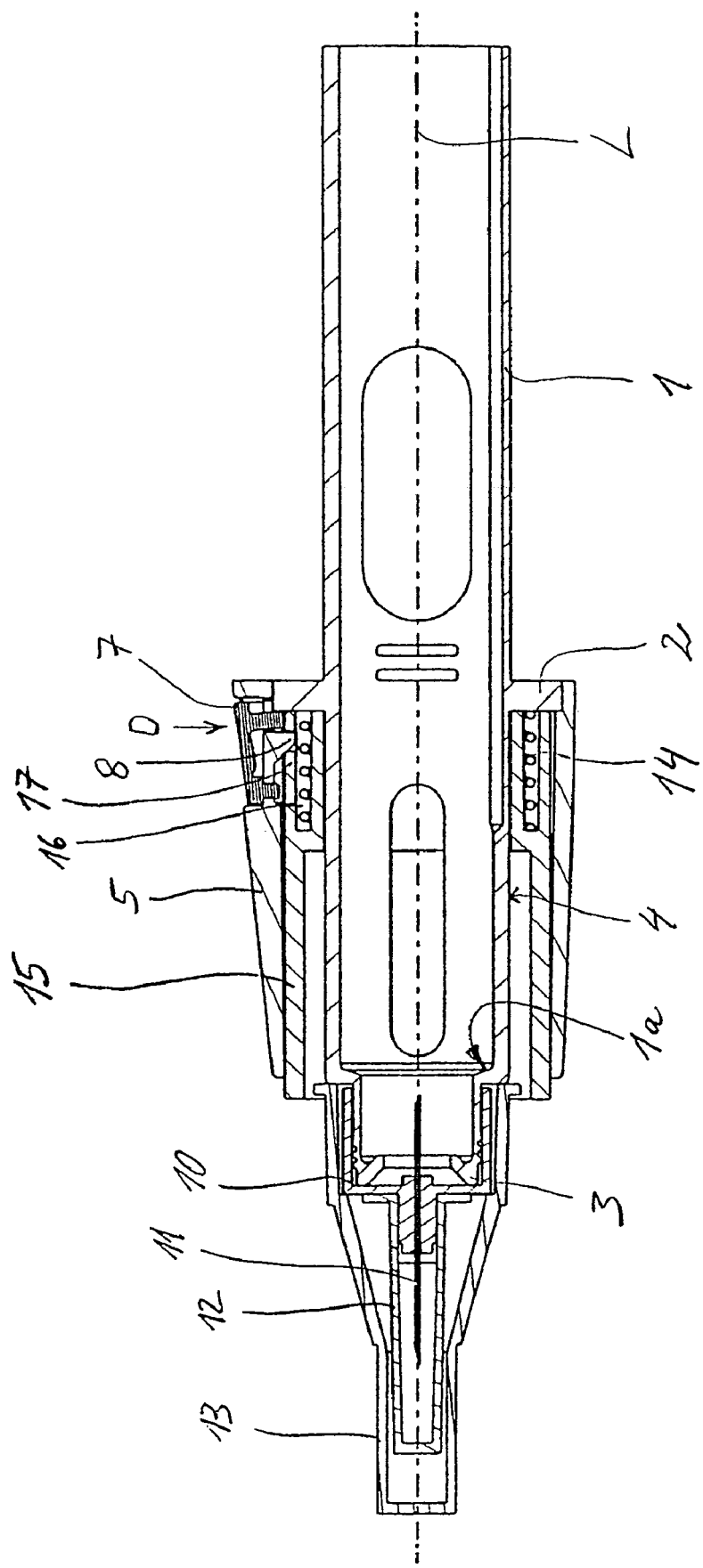
FIG. 2 shows the same part of the injection device when assembled, including an assembled needle cover, wherein a needle cover of the injection device is in an assembling position.

FIG. 1 shows a part, which may be referred to as the forward or front part, of an injection device in accordance with embodiments of the present invention, in an exploded view in which the separately produced components of the injection device are lined up along a central longitudinal axis L of the injection device, in an order suitable for being assembled. FIG. 2 shows the same components, once assembled.

The depicted part of the injection device includes a container holder 1 and a cladding structure 5 which when assembled, as for example can be seen from FIG. 2, form the forward part of a casing of the injection device. The forward part of the injection device further includes a needle cover 15, and a restoring means formed by a spiral spring 14 which when assembled is axially pressurized between the container holder 1 and the needle cover 15 in each axial position of the needle cover 15. As may be seen in FIG. 1 alone, but in particular in FIGS. 2 to 4, the needle cover 15 is accommodated, when assembled, in an annular space between a forward section of the container holder 1 and the cladding structure 5 surrounding said forward section, by the needle cover 15 protruding more or less deeply, depending on its axial position, into the annular space in the rearward direction.

Figure 8:
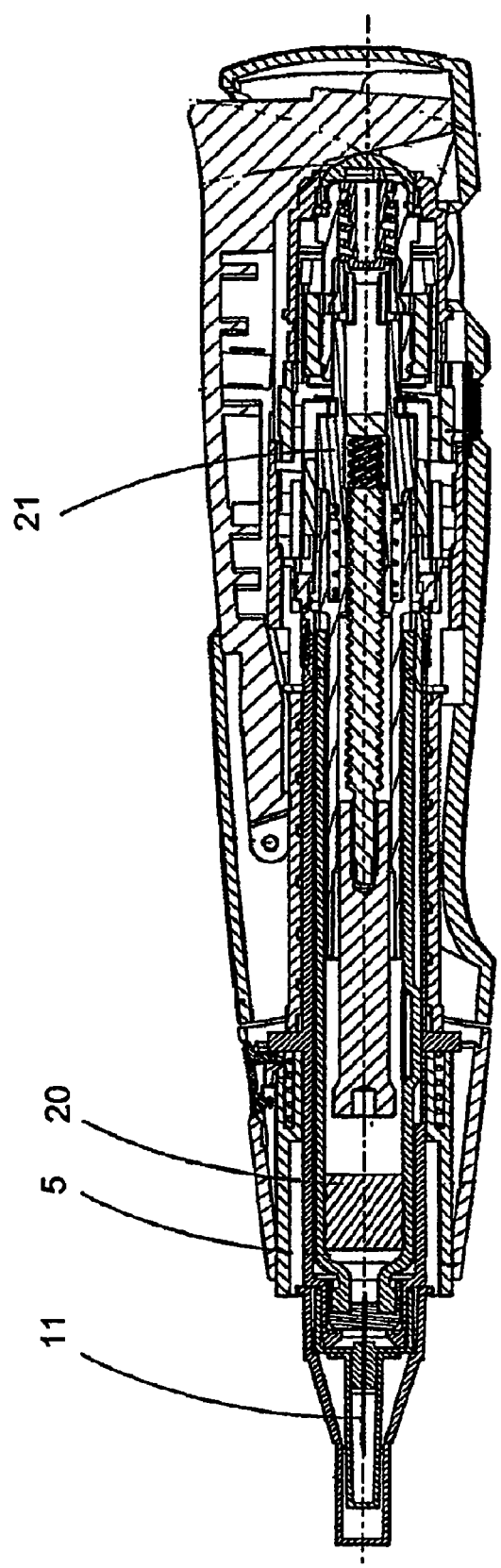
FIG 8. is a cross-section through an embodiment of an injection device depicting a piston and a piston rod.

The container holder 1 is substantially a cylindrical, in some preferred embodiments, a circular cylindrical, sleeve which forms a receptacle in its hollow cross-section for a container which contains a product to be injected. The container can be formed like known medicine ampoules such as are known from diabetes therapy for accommodating insulin or also in other therapies, for example osteoporosis therapy. As can be seen from FIG. 2, the container holder 1 forms a collar 1a in the region of its end 3, said collar 1a protruding radially inwards in the accommodating chamber and serving as a stopper for the product container to be inserted. Furthermore, the accommodating chamber forms an axial sliding guide for the container, which simultaneously also prevents tipping movements by the inserted container. The container holder 1 exhibits a narrower cross-section at one end 3 than in its other section. It is provided at the end 3 with an outer thread for a screw connection to a needle holder 10. It is provided at its other end with another outer thread which serves as a connection to a casing part of the injection device. The casing part mounts a conveying means for conveying the product and a dosing means, meshed with the conveying means, for pre-setting a product dosage which may be delivered by means of the conveying means. FIG. 8 shows, as an example of conveying means, a piston 20 in the container and a piston rod 21, axially facing a rear side of the piston 20, other Suitable conveying means and dosing means are sufficiently known and therefore do not need to be described separately. A circumferential collar 2 of the container holder 1, projecting outwards, serves to support the spring 14 in the rearward direction.

The needle holder 10 which may be affixed to the front end 3 of the container holder 1 is cup-shaped, with a sleeve part which is open in one direction and at the other end forms a base through which an injection needle 11 axially protrudes. In order to connect the needle holder 10 to the injection needle 11 over a larger axial length than would correspond to the axial thickness of the base, a cylindrical continuation projects from the centre of the base on its side, through which the injection needle 11 also protrudes. The injection needle 11 is held fixedly by the base of the needle holder 10 and the cylindrical continuation. A needle section protrudes or extends freely from the end of the needle holder 10, i.e., from the cylindrical continuation, and comprises a needle tip. A rear needle section protrudes into the hollow cross-section of the sleeve part of the needle holder 10, forming a rear needle tip, as can best be seen in FIGS. 2 to 4. The needle holder 10 is provided with an inner protecting cap 12 and an outer protecting cap 13 by the manufacturer. The inner protecting cap 12 is plugged onto the cylindrical continuation of the needle holder 10. The outer protecting cap 13 is plugged onto the sleeve part of the needle holder 10. Once the outer protecting cap 13 has been removed, the injection needle 11 is still completely surrounded by the inner protecting cap 12 and thus protected from damage, and the user from a needle prick.

The needle cover is substantially formed as a cylindrical, in the exemplary embodiment, circular cylindrical, sleeve. It exhibits a smooth outer surface area and an inner surface area formed in two stages, as may be seen from an overview of the figures, for example FIGS. 1 and 2. In its hollow cross-section, the needle cover 15 widens from one section in one stage to a forward section. The forward and the rear section each comprise a cylindrical inner surface area. A swelling is thus obtained along the length of the rear section, in which an annular gap 16 is formed which is open in the rearward direction. When assembled, the annular gap 16 accommodates one section of the spring 14 and serves as an axial guide for the spring 14. When assembled, the spring 14 is pressurised between the annular collar 2 and the end of the annular gap 16 of the needle cover 15. The container holder 1 thus forms a rearward mount, namely the annular collar 2, and the needle cover 15 a front abutment, namely the end of the annular gap 16, for the spring 14. When assembled, the container holder 1 guides the needle cover 15 axially slidably. The linearly cylindrical section of the container holder 1, which in FIG. 1 is surrounded by the spring 14, serves as an axial sliding guide for the container holder 1. The guiding counter area is the surface inner area of the rearward section of the needle cover 15.

In the region of its rearward section, the needle cover 15 is provided with a locking element. A spring tongue 17 and a breach 18 of the spring tongue 17 combine to form the locking element. The spring tongue 17 is formed on the needle cover 15 as one piece. To form the spring tongue 17, two axial slits 19 are formed in an outer surface of the rear section of the needle cover 15, the slits 19 extending to at or near the end of the needle cover 15. The spring tongue 17 is elastically bendable in the radial direction and acts as a bending beam fixedly clamped on one side, namely at its forward end.

The cladding structure 5 forms a locking counter element 8 which, as may be seen in FIG. 2, protrudes into the breach 18 in an end position of the needle cover 15 and locks the needle cover 15 against moving in the forward direction, by a positive lock. The spring tongue 17 with its breach 18 and the locking counter element 8 are thus in a locking mesh or connection, based on a positive lock, in the rearward end position of the needle cover 15. The positive lock is between a stopper area of the locking counter element 8, pointing in the rearward direction, and a counter stopper area, pointing in the forward direction and facing said stopper area, which forms the spring tongue 17 in the breach 18.

The locking counter element 8 is rigid, i.e. inflexible, with respect to the locking mesh. The locking mesh can, however, be released due to the elastic flexibility of the locking element, by elastically bending the locking element radially inwards, out of the locking mesh.

For releasing the lock, i.e., bending away the locking element, in some embodiments, the injection device includes an unlocking element 7. The unlocking element 7 is inserted into a recess 6 which the needle cover 15 comprises on its surface outer area and protrudes through a breach 9 formed in the region of the recess 6. The unlocking element 7 comprises a pressure operating area pointing outwardly and a projecting continuation with which it protrudes radially inwardly through the breach 9 after it has been inserted into the recess 6. The cladding structure 5 forms the breach 6 at a location such that the breach 6 is radially arranged above the locking element when the injection device is assembled. The breach 9 is furthermore formed such that, when assembled, it comes to rest radially above an end section of the spring tongue 17. In the exemplary embodiment, the forward end section of the spring tongue 17 is still situated forward of the breach 18, such that the entire axial length of the spring tongue 17 is available for elastically bending away and the radial pressure force of the unlocking element 7 necessary for bending away is as small as possible.

In order to assemble the injection device, the container holder 1 and the cladding structure 5 are connected to each other in the arrangement shown, for example, in FIG. 2, such that the annular space for the needle cover 15 is obtained between them. The annular space is closed off in the rearward direction by the annular collar 2 and is open in the forward direction. The needle cover 15, together with the spring 14 inserted in the annular gap 16 of the needle cover 15, is then slid into the annular space formed between the container holder 1 and the cladding structure 5, up to the rearward end position shown in FIG. 2. As it is slid in, the spring tongue 17 slides along the locking counter element 8 and is thus elastically bent away, radially inwards, until the breach 18 radially overlaps the locking counter element 8. As soon as the overlap is established, as is the case in the rearward end position of the needle cover 15, the spring tongue 17 elastically latches back again, radially outwards, and the cooperative lock shown in FIG. 2 is established.

Before the needle cover 15 is slid on, the unlocking element 7 is inserted into the recess 6 of the cladding structure 5, such that the continuation of the unlocking element 7 protrudes through the breach 9. The connection between the unlocking element 7 and the cladding structure 5 can be a frictional lock alone, but in some preferred embodiments, it may comprise a clip connection at an axial end of the unlocking element 7. In its connection to the cladding structure 5, the unlocking element 7 is clamped on one side like an elastic bending beam. The continuation, which protrudes radially inwards through the beach 9, is formed at the free end of said bending beam or unlocking element 7, and co-operates with the locking element of the needle cover 15 for the purpose of releasing the locking mesh. It may be seen from FIG. 2 how the unlocking element 7 is affixed in the manner of a bending beam. "D" indicates a pressure force using which the unlocking element 7 can be operated, radially inwards, in order to release the lock. The continuation of the unlocking element 7, which acts on spring tongue 17 to release the locking mesh, has no contact with the spring tongue 17 when the unlocking element 7 is at rest, i.e., is not being operated, but exhibits a small radial distance from it.

After the front part of the injection device shown has been connected to a rear part of the injection device which carries or houses the conveying means and the dosing means, the device may be shipped and is substantially ready for use. The user has only to insert a container filled with the product to be injected into the container holder 1 and to assemble the needle holder 10. This can be in the course of using the device for the first time or, for example, each time a used container is exchanged. The needle holder 10 can also be exchanged independently of exchanging the container.

In its assembling position, i.e., rearward end position, the front end of the needle cover 15 is sufficiently short of the end 3 of the container holder 1 that the needle holder 10 which the user grips in the region of its sleeve part can comfortably be connected to the container holder 1 by hand. Ideally, the needle cover 15 is at least sufficiently short of the end 3 of the container holder 1 that it allows lateral access to the needle holder 10 at least over the majority of the axial length of its sleeve part, when the needle holder 10 is connected to the injection device. Accordingly, as can be seen in FIG. 2, the needle cover 15 is accommodated in an annular space formed between the cladding structure 5 and container holder 10 over a majority of the axial length of the needle cover 15. To detach the needle holder 10, it can thus be gripped in the connecting region to the container holder 1, in the exemplary embodiment in the region of the screw thread in the threaded mesh. When the needle holder 10 is assembled, the rear needle section of the injection needle 11 pierces a sealing element which seals an end of the product container accommodated in the container holder 1. Assembling the needle holder 10 automatically fluidically connects the injection needle 11 to the interior of the product container. Since the forward end position of the needle cover 15 has been selected such that when the needle cover 15 is assembled, the needle holder 10 can be assembled on the injection device and disassembled from the injection device, the forward end position is referred to in the following as the assembling position of the needle cover 15. Once the needle holder 10 has been assembled, and still in the assembling position of the needle cover 15, the inner protecting cap 12 and the outer protecting cap 13 are removed from the needle holder 10, such that the injection needle 11 is exposed. Once the protecting caps 12 and 13 have been removed, the locking mesh of the locking elements is released by pressure-operating the unlocking element 7 in the direction of the force arrow D, such that the needle cover 15 is moved in the forward direction up to a stopper, into its protecting position, by the influence of the elasticity force of the tensed spring 14. With the needle cover 15 situated in its protecting position, the injection device is then ready for an injection.

Figure 3:
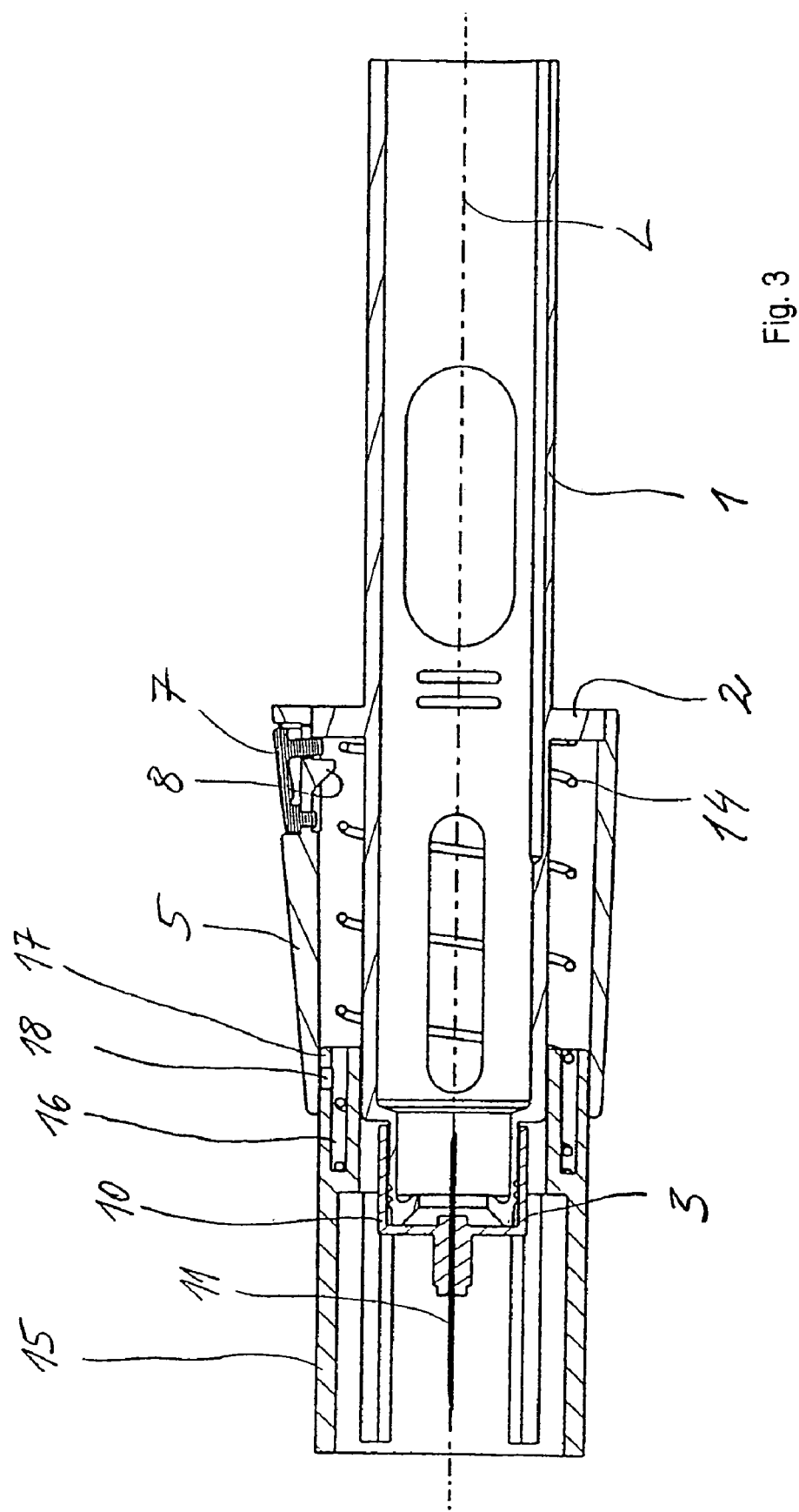
FIG. 3 shows the same part of the injection device, wherein the needle cover is in a protecting position.

FIG. 3 shows the injection device with the needle cover 15 situated in its protecting position. In the protecting position, the needle cover 15 protrudes beyond the tip of the injection needle 11. In the protecting position, the needle cover 15 can be locked against retracting in the rearward direction, such that it reduces unintentional access to the injection needle 11 from the side and thus damage to the injection needle 11 and danger of injury from the injection needle 11. If, in the protecting position, the needle cover 15 is locked against retracting, this locking mesh can however be released, in order to perform an injection. If a locking mesh is not provided in the protecting position and the needle cover in this case only serves as a blind, the injection device with the needle cover 15 situated in such a protecting position is immediately ready for a subsequent injection.

For the injection, the user selects the product dosage to be injected by means of the dosing means. The dosing means and the conveying means are connected such that the selected dosage predetermines the product dosage which may be delivered in the next injection. After the dosage has been selected, the injection device is placed onto the injection point via the forward end of the needle cover 15. By then pressing in the forward direction, the injection device is moved in the forward direction relative to the needle cover 15. In the course of this movement, the needle cover 15 slides on the sliding guide formed by the container holder 1 into the annular space between the container holder 1 and the cladding structure 5 and, conversely, the injection needle 11 advances in the forward direction beyond the needle cover 15, into the body tissue. The injection movement of the injection needle 11 is completed when the forward end of the needle holder 10 comes into contact with the surface of the skin, and the rear end of the needle cover 15 and the rear end of the needle holder 10 are correspondingly axially at the same location. This state corresponds to the injection position of the needle cover 15.

Figure 4:
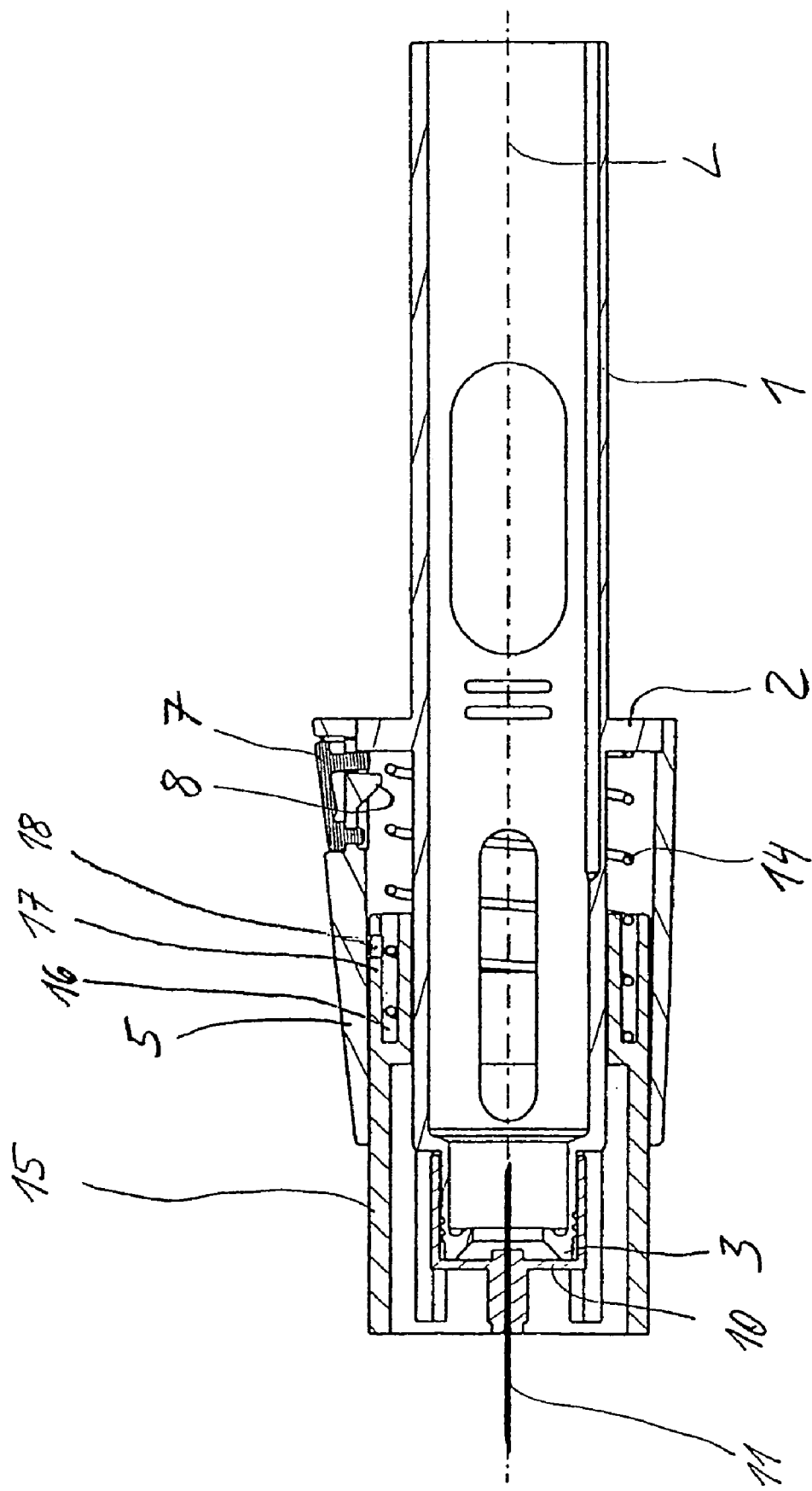
FIG. 4 shows the same part of the injection device, wherein the needle cover is in an injection position.

FIG. 4 shows the injection device with the needle cover 15 situated in its injection position. The injection needle 11 protrudes beyond the needle cover 15 to the extent of its entire, free forward needle section. In the case of the injection described, it protrudes into the body tissue. The selected product dosage is then administered, by the user—for example, a patient him or her self—operating the conveying means. The conveying means can include a piston 20 accommodated in the container such that it can move axially in the forward direction and a piston rod 21 acting on the piston 20 as shown in FIG. 8. Correspondingly, in order to deliver or administer product, the user presses the piston rod 21 in the forward direction and consequently advances the piston 20 by a length predetermined by the elected dosage, thus delivering the selected product dosage from the container and administering it through the injection needle 11. After the product dosage has been administered, the injection needle 11 is removed from the body tissue. Since the needle cover 15 is held in the injection position by the forces acting against each other on the needle cover 15, namely the elasticity force of the spring 14 and the pressure force acting against it, when the pressure force abates, the needle cover 15 moves in the forward direction back into the protecting position under the influence of the spring 14.

If the injection needle 11 is to be exchanged, the needle cover 15 is pressed beyond the injection position, back into the assembling position. In the last part of this movement, after the needle cover 15 has already been moved beyond the injection position in the rearward direction, the rear end of the spring tongue 17 comes into contact with the locking counter element 8. The locking counter element 8 is tapered radially inwards on its side pointing in the forward direction, in the exemplary embodiment, its forward side simply points obliquely with respect to axial. By tapering the locking counter element 8, the spring tongue 17 can slide along the locking counter element 8 via its rear end and is thus continuously bent away radially inwardly. As soon as the breach 18 draws axially level with the locking counter element 8, the spring tongue 17 latches back radially outwards again due to its inherent elasticity force and the locking mesh shown in FIG. 2 is established. The needle holder 10 is again freely accessible from the side. Before disassembling the needle holder 10, at least one of the two protecting caps 12 and 13 should be plugged onto the needle holder 10, in order to prevent injuries from the injection needle 11. Only then should the needle holder 10, or as applicable the protecting cap 13 seated on the needle holder 10, be gripped and the needle holder 10 detached from the injection device.

Figure 5:
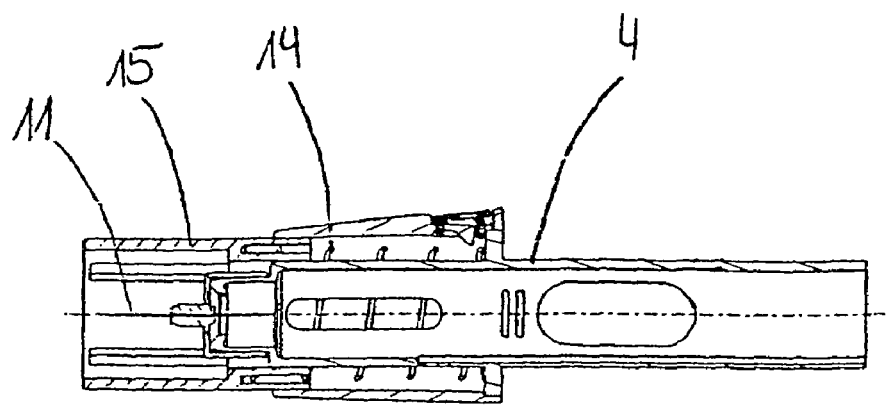
FIG. 5 is a partial cross-section of an embodiment of an injection device comprising needle protector in accordance with embodiments of the present invention, in an advanced position.
Figure 6:
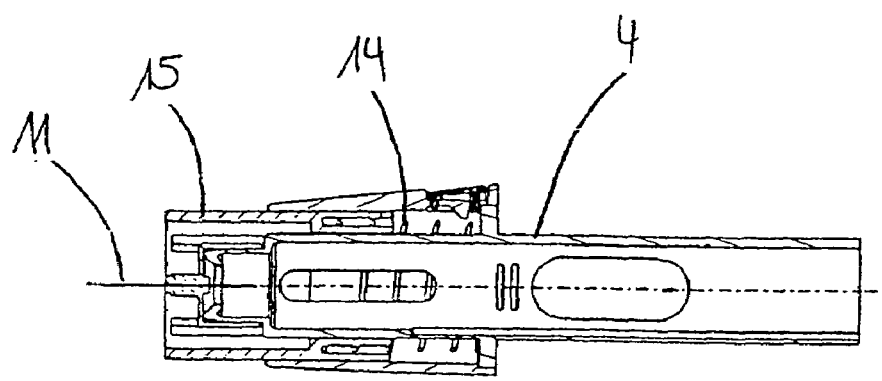
FIG. 6 is a partial cross-section of the embodiment of the injection device shown in FIG. 5, in a retracted position.
Figure 7:
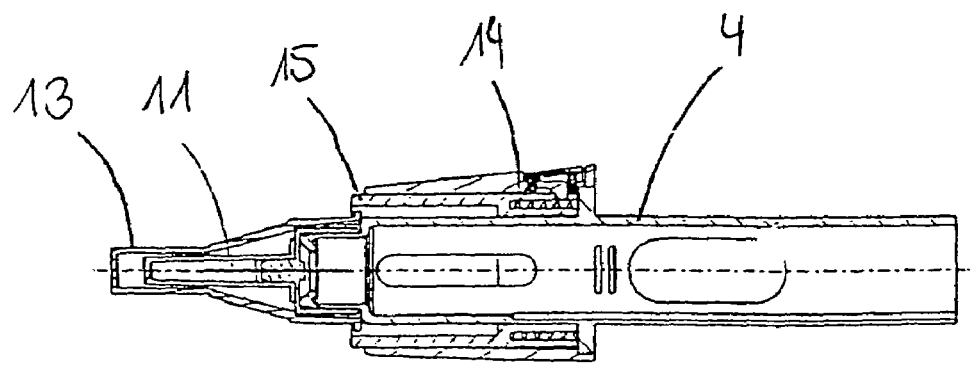
FIG. 7 is a partial cross-section of an embodiment of an injection device comprising needle protector and a needle cap.

FIGS. 5-7 also show an embodiment of an injection device comprising a needle protector or cover in accordance with embodiments of the present invention. The needle cover is formed by the needle cover 15 which is arranged on the receptacle in form of a holder 4 for a product container, such that it can be shifted. Other arrangements of the sleeve are possible. FIG. 5 shows the needle cover 15 in an advanced position in which it completely surrounds the injection needle 11 in the circumferential direction. The holder 4, together with the needle cover 15, can be inserted into the cladding structure 5 forming a casing of the injection device, and removed again from the casing 5 in order to exchange a product container. The injection needle 11 then remains protected by the sleeve 15 during the entire exchanging process. The needle cover 15 is held in the advanced position by a spiral spring 14, but can be shifted into a rear position, in which the injection needle 11 is exposed, as shown in FIG. 6, by applying a force along the holder 4. To administer a product, the injection device is placed vertically on a surface at the injection point. When the injection needle 11 is pushed into the surface, the needle cover 15 is retracted in the longitudinal direction of the holder and the injection needle can penetrate the surface. After the injection device is removed from the surface, the needle cover 15 is returned to the advanced position again by the spiral spring 14. The injection needle therefore remains protected by the sleeve from exterior access during the entire administering process.

For exchanging the injection needle for a subsequent injection, a needle cap 13 serving as protecting cap can be placed onto the opening of the needle cover 15. When the needle cap is pushed in the longitudinal direction onto the injection device, the needle cover 15 serves as a guide for the needle cap 13 onto the injection needle until the cap is accommodating the needle within itself. The injection needle, together with the needle cap 13, can then be removed from the injection device. A new injection needle in another needle cap can correspondingly be placed onto the injection device by attaching the new needle cap to the needle cover 15 and guiding it towards the holder 4 or the product container using the needle cover 15, until it is fixed on it. The needle cover 15 is then shifted into a rear position. The injection needle remains protected, either by the sleeve or the needle cap, during the entire process of exchanging the injection needle and the process of exchanging a product container. Pricking injuries can therefore largely be prevented.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising a needle cover, said injection device comprising:
   a) a casing comprising a container holder for a container containing an injectable product, and a cladding structure which surrounds at least an axial section of said needle cover when the needle cover is in a locking assembling position;
   b) a piston in the container, wherein a stroke of the piston delivers the injectable product, and a piston rod axially faces a rear side of the piston;
   c) a needle holder comprising an injection needle which is or can be connected fluidically to the container by means of said needle holder;
   d) said needle cover carried by said casing;
   e) a spring effectively acting between said casing and said needle cover, said spring providing a elasticity force for moving said needle cover forward into a non-locking protecting position;
   f) wherein the needle cover carried by the casing is movable against the elasticity force of the spring from the non-locking protecting position, past a non-locking injection position, into the locking assembling position;
   g) wherein, in said non-locking protecting position the needle cover extends beyond a needle tip of said injection needle, and in said non-locking injection position, is short of said needle tip;
   h) wherein, in said locking assembling position, the needle cover allows access to the needle holder, such that the needle holder can be gripped and connected to or detached from the casing;
   i) wherein the casing comprises a first locking element and the needle cover comprises a second locking element, said locking elements in a locking connection in the locking assembling position of the needle cover, said locking connection preventing the needle cover from moving past the non-locking injection position into the non-locking protecting position by the elasticity force of the spring; and
   j) wherein the container holder and the cladding structure are connected such that they form an annular space, which accommodates the needle cover over the majority of its axial length when the needle cover is in the locking assembling position.

2. The injection device as set forth in claim 1, wherein in the locking assembling position, the needle cover is short of a forward end of the needle holder in the rearward direction.

3. The injection device as set forth in claim 1, wherein the needle holder is or can be connected to the casing.

4. The injection device as set forth in claim 1, wherein the casing comprises a container holder which forms an accommodating chamber for the container.

5. The injection device as set forth in claim 4, wherein the needle cover is supported on said container holder in the rearward direction.

6. The injection device as set forth in claim 4, wherein the container holder guides the needle cover.

7. The injection device as set forth in claim 1, wherein the casing forms a mount and the needle cover forms an abutment for said spring.

8. The injection device as set forth in claim 7, wherein one of said mount or said abutment axially guides the spring formed as a mechanical spiral pressure spring.

9. The injection device as set forth in claim 1, wherein the locking connection is based on a positive lock between the locking elements.

10. The injection device as set forth in claim 1, wherein at least one of the locking elements is moveable, against an elasticity force, out of the locking connection.

11. The injection device as set forth in claim 10, wherein the moveable locking element is elastic.

12. The injection device as set forth in claim 11, wherein said elastic locking element bends elastically.

13. The injection device as set forth in claim 1, further comprising an unlocking element operable to release the locking connection.

14. The injection device as set forth in claim 13, wherein said unlocking element is a push-key.

15. The injection device as set forth in claim 13, wherein the unlocking element presses against one of the locking elements to release the locking connection.

16. The injection device as set forth in claim 13, wherein the unlocking element acts on one of the locking elements through a breach formed in one of the casing or the needle cover.

17. The injection device as set forth in claim 1, wherein the needle cover is moved into the injection position by a pressure force acting in the rearward direction on a forward end of the needle cover and, when said pressure force abates, is automatically moved into the protecting position by the elasticity force.

* * * * *

UNITED STATES PATENT AND TRADEMARK OFFICE
CERTIFICATE OF CORRECTION

PATENT NO. : 7,566,324 B2
APPLICATION NO. : 11/404384
DATED : July 28, 2009
INVENTOR(S) : Edgar Hommann et al.

It is certified that error appears in the above-identified patent and that said Letters Patent is hereby corrected as shown below:

| Column | Line | | Should Read |
|---|---|---|---|
| 8 | 45 | "example of conveying means" | -- example of a conveying means -- |
| 8 | 46-47 | "piston 20, other Suitable conveying" | -- piston 20. Other suitable conveying -- |

CLAIMS

| Column | Line | | Should Read |
|---|---|---|---|
| 13 | 62 | "non-locking protecting positions" | -- non-locking protecting position, -- |

Signed and Sealed this

Twentieth Day of October, 2009

David J. Kappos
*Director of the United States Patent and Trademark Office*